United States Patent [19]
Anderson et al.

[11] Patent Number: 5,471,001
[45] Date of Patent: Nov. 28, 1995

[54] CRYSTALLIZATION OF ADIPIC ACID

[75] Inventors: Howard W. Anderson, Hockessin; John B. Carberry, Newark, both of Del.; Harold F. Staunton, Avondale, Pa.; Bhagya C. Sutradhar, Orange, Tex.

[73] Assignee: E. I. Du Pont de Nemours and Company, Wilmington, Del.

[21] Appl. No.: 356,758

[22] Filed: Dec. 15, 1994

[51] Int. Cl.$^6$ .............................. C07C 51/42; A44B 1/04; A44B 11/25
[52] U.S. Cl. .......................... 562/593; 562/513; 562/530; 560/179; 23/295 R
[58] Field of Search ................................... 562/593, 513, 562/530; 560/179, 208; 62/12, 538; 23/295 R, 297, 299, 301; 34/303; 210/280, 319, 320

[56] References Cited

U.S. PATENT DOCUMENTS

| | | | |
|---|---|---|---|
| 4,052,441 | 10/1977 | Brunner | 560/179 |
| 4,254,283 | 3/1981 | Mock | 562/530 |
| 4,650,507 | 3/1987 | Cheng et al. | 62/12 |
| 4,867,817 | 9/1989 | Kneafsey et al. | 156/73.1 |

*Primary Examiner*—Arthur C. Prescott

[57] ABSTRACT

Crystallization of adipic acid using low intensity ultrasonic agitation during crystallization results in purer product that is more readily handled. Apparatus for carrying out the process is also disclosed.

10 Claims, 1 Drawing Sheet

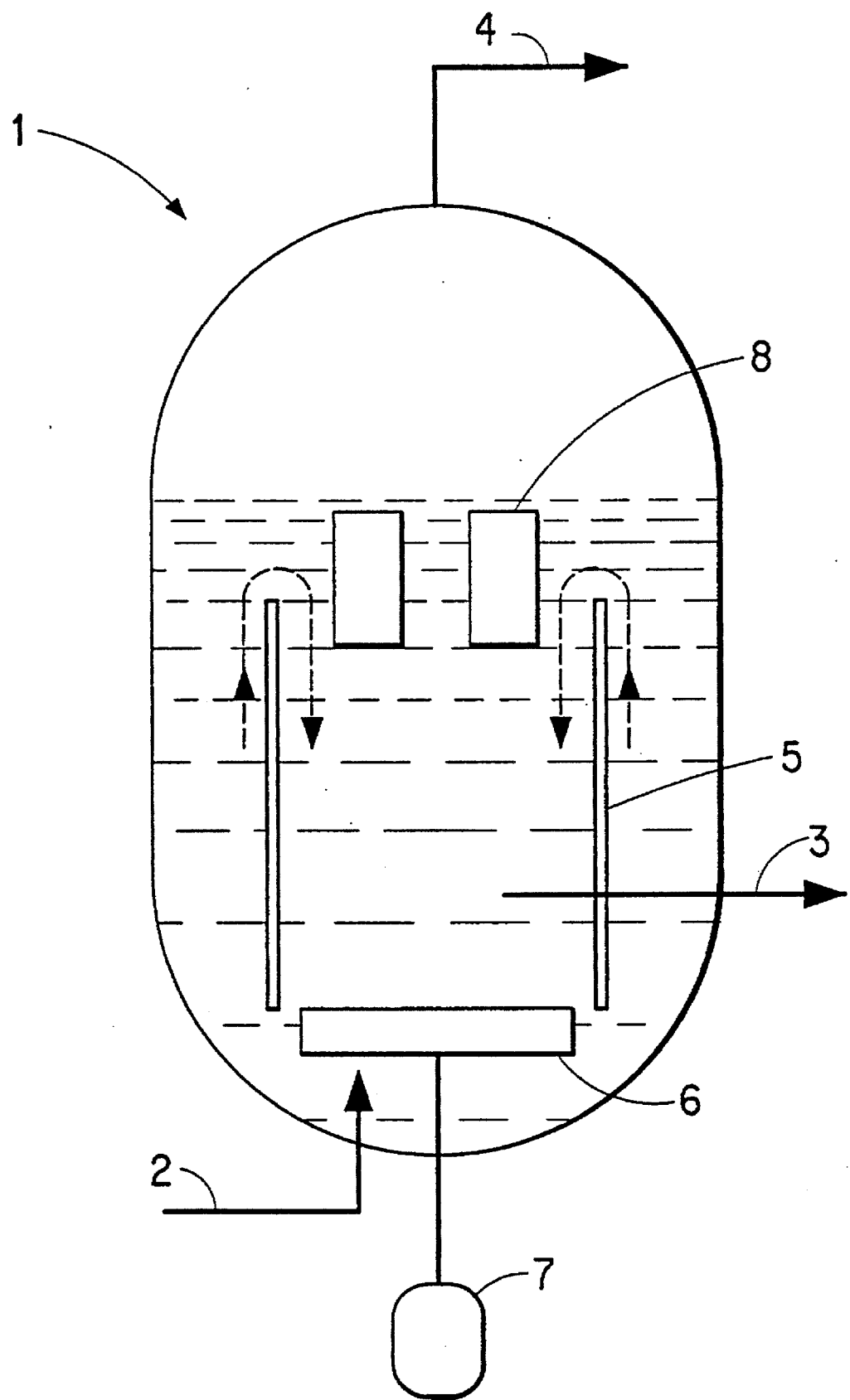

CRYSTALLIZATION OF ADIPIC ACID

FIELD OF THE INVENTION

This invention relates to the crystallization of adipic acid to produce a product in which the crystals are more uniform in shape, in size, in density, and in purity. The crystals produced by this invention have fewer inclusions of impurities, and are more easily handled than conventional adipic acid crystals. The desired crystals are obtained by crystallizing adipic acid while it is subjected to ultrasonic agitation. Preferably, at least some of the ultrasonic agitation is low intensity agitation. In a preferred embodiment the ultrasonic agitation includes some high intensity agitation. In a most preferred embodiment the mother liquor containing the nascent crystals of adipic acid is subjected to pulses of ultrasonic agitation. This invention also relates to an apparatus suitable for use in carrying out the process of the invention.

BACKGROUND OF THE INVENTION

In a commercial process for the manufacture of adipic acid, cyclohexanol and cyclohexanone are oxidized with nitric acid in the presence of copper and vanadium catalysts. The resulting product contains adipic acid, as well as glutaric acid, and succinic acid. Conventionally, most of the adipic acid is removed from the product by crystallization, and the remaining portion of the product has in the past been treated in various processes to recover other useful products and the copper and vanadium catalyst metals. For example, in U.S. Pat. No. 4,375,552 to Kuceski the stream after crystallization and removal of most of the adipic acid is treated with an alcohol to form esters which are not soluble in the aqueous phase. The esters are then removed from the stream, and the catalyst metals, which remain in the aqueous phase, are recycled to the nitric acid oxidation step.

Ultrasonic agitation of various fluids during crystallization is known, for example, see U.S. Pat. No. 3,892,539 (1975) which shows fluidized bed crystallization with supersaturated fluidizing liquid—and ultrasonic frequency agitation which fractures larger crystals for seeds. In "Effect of Cavitation on the Kinetics of Crystallization from Solution" by Hofman, J. and Roubik, V. in Chem. Prum., 44(1), 18–19, 1994: The effect of ultrasound on the kinetics of crystallization of potassium sulfate from aqueous solutions was studied. The crystal growth rate was found to be enhanced by ultrasound for crystals up to a certain size (approx. 350 microns).

"Rapid Crystallization using Ultrasonic Irradiation—Sonocrystallization" by David R. Kelly et al. in Tetrahedron Letters, 34(16), 2689–90, 1993: Used ultrasonic irradiation to induce rapid crystallization of materials which normally only crystallize with difficulty.

"The Narrowing of Crystal Size Distributions in a Sonicator-MSMPR Crystallizer System" by Mydlarz, J. and Briedis, D. in Chem. Eng. Commun., 104, 291–305, 1991: Use of sonication was found to narrow the crystal size distribution.

"Shape of Crystals During Slow Crystallization" by Shopova, R. in God. Vissh. Khim.-Tekhnol. Inst., Sofia, Vol. Date 1979, 26(2), 68–74, 1980: Ultrasound was found to favor growth of one type of surface but not others.

"Effect of Ultrasound on the Latent Period of Crystallization from Spersaturated Solutions" by Kortnev, A. V. and Martynovskaya, N. V. in Sb., Mosk. Inst. Stali Splavov, 77, 98–100, 1974: Ultrasound was found to influence nucleation rate—increasing ultrasonic energy decreased induction period.

SUMMARY OF THE INVENTION

The present invention is a process for the crystallization of adipic acid which comprises subjecting an aqueous based mother liquor containing dissolved adipic acid and nascent crystals of adipic acid to low intensity ultrasonic agitation while cooling the mother liquor and/or decreasing the solvent (water) content of the mother liquor.

The present invention is also an apparatus comprising a vertically mounted cylindrical container, a cylindrical hollow baffle mounted in said container and spaced equidistant from the cylindrical wall of the container, said baffle being also spaced from the bottom and top of the container, means located near the lower end of the cylindrical container for moving mother liquor contained in the cylindrical hollow baffle downwardly, where the mother liquor is diverted by the bottom of the cylindrical container and forced to pass between the inner wall of the cylindrical container and the cylindrical hollow baffle and then over the top of the baffle, and transducer means located in the upper portion of the cylindrical container for transmitting to the mother liquor low energy ultrasonic agitation.

DESCRIPTION OF THE DRAWING

The drawing is a cross-sectional view of an apparatus suitable for use in carrying out the process of the invention.

DETAILED DESCRIPTION

Use of low intensity power ultrasound in adipic acid crystallization from aqueous based mother liquor leads to product crystals with smooth surfaces and with fewer inclusions and voids, and the product has low moisture content and pours more readily.

Pulsed sonication is as effective as continuous sonication for all the above benefits. This allows a significant power-saving. Also, pulsed sonication makes it possible to apply sonication in large crystallizers.

Sonicating a large crystallizer (several thousand gallons) is extremely difficult. However, this difficulty is overcome by the use of the apparatus shown in the drawing, where there is a continuous recirculation of slurry (i.e., aqueous based mother liquor containing dissolved adipic acid, nascent crystals of adipic acid, and crystals of adipic acid) through the cylindrical baffle or draft tube in the crystallizer. Only one zone, the zone above the draft tube is sonicated; this is equivalent to pulse-sonicating the entire crystallizer.

Use of ultrasonic agitation in refined crystallization produces adipic crystals with better flowability and with less tendency to cake during storage/transportation, making it easier to load and unload the product. Adipic acid crystals produced by the process of the invention, because of fewer and/or smaller inclusions and voids make it easier to dry the product, i.e., less energy is required because less water is entrained in the crystals. The process of the invention also reduces fouling in the crystallizers—it takes longer for crystals to form on the walls of the baffle and container walls.

DETAILED DESCRIPTION OF THE DRAWING

In the drawing the crystallizer consists of a cylindrical container 1 having a top and bottom. The container has an inlet conduit 2 for the introduction of aqueous mother liquor containing dissolved adipic acid, and an outlet conduit 3 for the removal of product, i.e., an aqueous mixture of adipic acid crystals. The crystallizer also has an outlet conduit 4 attached to a vacuum pump where vapors are taken off the liquid at a pressure less than atmospheric pressure. Evaporation under reduced pressure reduces the temperature of the liquid, and lowers the amount of solvent (water) in the aqueous mother liquor; both of these factors lead to crystallization of the adipic acid. The container contains a cylindrical baffle or draft tube 5 mounted equidistant from the cylindrical sides of the container 1. An impeller 6 is located centrally near the bottom of the container to draw liquid in the container through the center of the cylindrical baffle which is then deflected by the bottom of the container and moved between the baffle wall and the container wall. The impeller is driven by prime mover 7, for example, an electric motor. In the upper portion of the container is located an ultrasonic generating means 8, i.e., a transducer or an number of transducers. In operation the ultrasonic generating means will be submerged in the mother liquor, but the upper portion the container will normally be filled with vapor.

"Low intensity ultrasonic agitation" means not more than about 1.0 watt/cm2 of power.

"High intensity ultrasonic agitation" means more than about 1.0 watt/cm2.

In an adipic acid plant, the aqueous mother liquor containing adipic acid from the oxidation of cyclohexanol and cyclohexanol with nitric acid is passed through a series of crystallizers. The crystals of adipic acid recovered from first crystallizer are dissolved in hot water, and this new aqueous mother liquor is crystallized in a second crystallizer. In the final crystallizer in the series the aqueous mother liquor is subjected to the ultrasonic agitation of the invention. The hot mother liquor contains about 20 to 50% by weight adipic acid. The usual temperature of the mother liquor entering the final crystallizer is about 95 degrees C. In the crystallizer the temperature is lowered by evaporation and/or conventional cooling devices which may be in the wall of the crystallizer or located externally, which causes crystallization to begin. The mother liquor is agitated ultrasonically with low energy agitation. When the mother liquor reaches about 55 degrees C., the crystallization is completed. The evaporation of the mother liquor is hastened by lowering the pressure above the mother liquor. A suitable pressure is about 110 millimeters of mercury. The mother liquor may be treated in the final crystallizer as a batch but preferably is treated continuously. The residence time in the final crystallizer will depend on, among other things, the temperature of the mother liquor when it enters and the pressure. Usually the mother liquor will reside in the final crystallizer about one hour. In a preferred embodiment, where a crystallizer of the type shown in the drawing is employed, the mother liquor is constantly circulated and periodically passed through a zone of ultrasonic agitation. In a preferred embodiment, a part of the mother liquor will pass through the zone of ultrasonic agitation about once every 5 to 20 seconds.

The low intensity ultrasonic agitation employed in the present invention will normally be in the range of about 0.001 to 1.0 watts per square centimeter of radiating surface of the transducer. The source of the ultrasonic agitation can be an electromagnetic, piezoelectric electrostrictive, or magnetostrictive device. Such devices are known in the art and are called transducers.

The low intensity ultrasonic agitation does not usually fragment well formed crystals, but instead displaces crystal fragments that have begun to grow on well formed crystals. High energy ultrasonic agitation will fragment even well formed crystals. It may be desirable under certain circumstances to employ high intensity ultrasonic agitation at the beginning of the crystallization to produce good quality nuclei (nascent crystals) and then lower the energy level to low intensity ultrasonic agitation as the crystallization is continuing to induce more perfect crystal growth.

EXAMPLE 1

Prepare feed solution as follows:

280 g Adipic acid+420 g water; heat to dissolve adipic acid (approx. 90 degrees C.) and then quickly transfer to the crystallizer.

(1) Cool down to 60 degrees C. under vacuum (145 mm Hg abs) under sonication (40 kHz, applied intensity approx. 0.1 watts/cm2) and 450 rpm agitation. Filter hot, air dry for size analysis. Vacuum oven dry for water analysis.

(2) Repeat (1) without sonication.

TABLE I

| | Particle Size and Moisture Content Data | |
|---|---|---|
| Sample | Wt. Av. Size. in Microns | % H2O |
| 1 | 215 | 0.108 |
| 2 | 207 | 0.122 |

A 12% reduction in water content was observed in the sonicated case.

EXAMPLE 2

Prepare feed solution as follows:

180 g adipic acid (AA)+320 g. demineralized water; heat to dissolve AA (approx. 90 degrees C.) and then quickly transfer to the crystallizer.

(1) Adjust the sonic bath (40 kHz) temp. at 58 degrees C. Turn ON sonicator (applied intensity approx. 0.05 watts/cm2) and vacuum (19.5 in. Hg). Turn agitator ON (500 rpm). Allow to cool down under vacuum to 60 degrees C. Transfer the slurry quickly and filter hot. Air dry sample for size analysis. Conventional oven dry (105 degrees C. for 2 hr.) for water analysis.

(2) Repeat (1) above with pulsed sonication as: sec. ON+10 sec. OFF.

TABLE II

| | Particle size and Moisture Content Data | |
|---|---|---|
| Sample | Wt. Ave. Size in Microns | % H2O |
| 1 | 285 | 0.067 |
| 2 | 290 | 0.056 |

This example demonstrated that pulsed sonication is at least equally beneficial as continuous sonication for improving crystal quality in refined AA crystallization.

EXAMPLE 3

Control Example (A) 160 g of adipic acid was dissolved in 240 g demineralized water (by heating and stirring at approximately 95 degrees C. The solution was allowed to cool down and crystallize under mechanical stirring (500 rpm). The crystallization was stopped when the temperature reached 55 degrees C. and the slurry was filtered hot. The filter cake was air-dried and size analyzed.

Invention Example (B) Another solution was prepared as in A. It was allowed to cool down to 55 degrees C. under ultrasonic vibration, 20 kHz, initial intensity in the range 2–4 Watts/cm2 and mechanical stirring (500 rpm). The slurry was filtered hot, air-dried, and size analyzed.

Estimated intensity after crystallization began <1 watt/cm2. The cooling time in all the cases were approximately 15 min.

TABLE III

Particle Size of Samples in Example 3

| Sample | Wt. Ave. Size in Microns |
|---|---|
| A | 330 |
| B | 300 |

A microanalysis of the solid samples was performed and the results are presented in Table IV.

TABLE IV

Microanalysis of Samples A, B of Example 3

| Sample | Liquid Vol. % | Void Vol. % | Breaking Pres. (Relative) |
|---|---|---|---|
| A | 0.12 | 1.8 | 1400 |
| B | 0.06 | 1.0 | 1800 |

Liquid Vol. % is the estimated vol. % of liquid filled occlusions.

Void Vol. % is the estimated total internal void volume.

Break. Pres. is the crush strength of the crystals.

Clearly, ultrasonic vibrations improved crystal quality in strength and lowered the inclusion and void content. Also, high intensity at the beginning of crystallization (to produce nascent crystals) appears to be beneficial.

What is claimed is:

1. A process for the crystallization of adipic acid which comprise subjecting an aqueous based mother liquor containing dissolved adipic acid and nascent crystals of adipic acid to low intensity ultrasonic agitation while cooling the mother liquor and/or decreasing the water content of the mother liquor.

2. The process of claim 1 in which the nascent crystals are produced under high intensity ultrasonic vibration.

3. The process of claim 1 in which the mother liquor is circulated through a zone where it is subjected to periodic pulses of low intensity ultrasonic agitation.

4. The process of claim 1 in which the mother liquor also contains crystals of adipic acid.

5. The process of claim 1 in which the low intensity ultrasonic agitation is at a frequency of 20 to 100 kHz.

6. A process of claim 3 in which the mother liquor passes through the zone where it is subjected to low intensity ultrasonic agitation once about every 5 to 20 seconds.

7. The process of claim 6 in which the mother liquor is subjected to about 200 to 300 exposures to ultrasonic agitation in one hour.

8. The process of claim 7 in which water in the mother liquor is removed as vapor at a pressure less than atmospheric pressure.

9. An apparatus comprising: (a) a vertically mounted cylindrical container having a cylindrical wall, a top, and a bottom, (b) a cylindrical hollow baffle mounted in said container and spaced equidistant from the cylindrical wall of the container, said baffle being also spaced from the bottom and top of the container, (c) means located near the lower end of the cylindrical container for moving mother liquor contained in the cylindrical hollow baffle downwardly, where the mother liquor is diverted by the bottom of the cylindrical container and forced to pass between the inner wall of the cylindrical container and the cylindrical hollow baffle and then over the top of the baffle, and (d) transducer means located in the upper portion of the cylindrical container for transmitting to the mother liquor low energy ultrasonic agitation.

10. The apparatus of claim 9 in which the means for moving mother liquor is an impeller.

* * * * *